(12) United States Patent
Kang et al.

(10) Patent No.: US 9,772,296 B2
(45) Date of Patent: Sep. 26, 2017

(54) METHOD OF INSPECTING A SURFACE OF A SUBSTRATE AND APPARATUS FOR PERFORMING THE SAME

(71) Applicant: Samsung Electronics Co., Ltd., Suwon-Si, Gyeonggi-Do (KR)

(72) Inventors: Byung-Bok Kang, Yongin-si (KR); Seok-Min Kang, Hwaseong-si (KR); Bon-Ok Koo, Hwaseong-si (KR); Kyoung-Hwan Kim, Yongin-si (KR); Myung-Woo Kim, Yongin-si (KR); In-Gi Kim, Hwaseong-si (KR); Hyun-Chul Kim, Seoul (KR); Sung-Ki Roh, Hwaseong-si (KR); Gyung-Jin Min, Seongnam-si (KR); Eun-Seok Lee, Hwaseong-si (KR); Jin-Suk Hong, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 421 days.

(21) Appl. No.: 14/460,814

(22) Filed: Aug. 15, 2014

(65) Prior Publication Data
US 2015/0116698 A1 Apr. 30, 2015

(30) Foreign Application Priority Data
Oct. 31, 2013 (KR) ........................ 10-2013-0130794

(51) Int. Cl.
*G01N 21/95* (2006.01)
*G01N 21/88* (2006.01)

(52) U.S. Cl.
CPC ..... *G01N 21/9501* (2013.01); *G01N 21/8851* (2013.01); *G01N 2021/8887* (2013.01)

(58) Field of Classification Search
CPC ........... G01N 21/9501; G01N 21/8851; G01N 2021/8887
See application file for complete search history.

(56) References Cited

U.S. PATENT DOCUMENTS

| | | | | |
|---|---|---|---|---|
| 5,274,434 A | * | 12/1993 | Morioka | ................ B82Y 15/00 257/E21.525 |
| 5,644,393 A | * | 7/1997 | Nakamura | ......... G01N 21/9501 250/559.45 |
| 5,912,732 A | * | 6/1999 | Sekine | ................... G01N 21/94 356/237.4 |
| 5,917,601 A | * | 6/1999 | Shimazaki | ............. G01D 5/342 356/400 |

(Continued)

FOREIGN PATENT DOCUMENTS

| | | |
|---|---|---|
| JP | 2013019780 A | 1/2013 |
| JP | 2013083491 A | 5/2013 |

(Continued)

*Primary Examiner* — Kara E Geisel
*Assistant Examiner* — Dominic J Bologna
(74) *Attorney, Agent, or Firm* — Harness, Dickey & Pierce, P.L.C.

(57) ABSTRACT

In a method of inspecting a surface of a substrate, a first surface image of the substrate before loaded into a process chamber may be obtained. The first surface image may be processed to detect a defect on the surface of the substrate. Thus, the surfaces of all of the substrate may be inspected during a process may be performed without transferring the substrates.

14 Claims, 7 Drawing Sheets

(56) References Cited

U.S. PATENT DOCUMENTS

| | | | |
|---|---|---|---|
| 6,020,957 A * | 2/2000 | Rosengaus | G01N 21/9501 356/237.4 |
| 6,813,032 B1 * | 11/2004 | Hunter | G01N 21/8903 250/559.22 |
| 6,845,292 B2 * | 1/2005 | Sha | H01L 21/67259 414/936 |
| 6,954,268 B2 | 10/2005 | Naiki et al. | |
| 7,307,725 B2 | 12/2007 | Oomori et al. | |
| 8,098,412 B2 | 1/2012 | Kagami | |
| 8,602,716 B2 * | 12/2013 | van der Meulen | H01L 21/67161 414/805 |
| 2003/0202865 A1 * | 10/2003 | Ponnekanti | H01L 21/67742 414/217 |
| 2010/0074515 A1 | 3/2010 | Zhao et al. | |
| 2012/0225518 A1 * | 9/2012 | De Santi | H01L 21/67736 438/73 |
| 2013/0044316 A1 | 2/2013 | Gastaldo et al. | |

FOREIGN PATENT DOCUMENTS

| | | |
|---|---|---|
| JP | 2013527925 A | 7/2013 |
| KR | 101130209 B1 | 4/2004 |
| KR | 20040039372 A | 5/2004 |
| KR | 20060046192 A | 5/2006 |
| KR | 20100070966 A | 6/2010 |
| KR | 100989561 B1 | 10/2010 |
| KR | 101001113 B1 | 12/2010 |
| KR | 101060653 B1 | 8/2011 |
| KR | 20110119079 A | 11/2011 |
| KR | 20120006860 A | 1/2012 |
| KR | 20120127220 A | 11/2012 |
| KR | 101236286 B1 | 2/2013 |
| KR | 20130051796 A | 5/2013 |
| KR | 20130059262 A | 6/2013 |

* cited by examiner

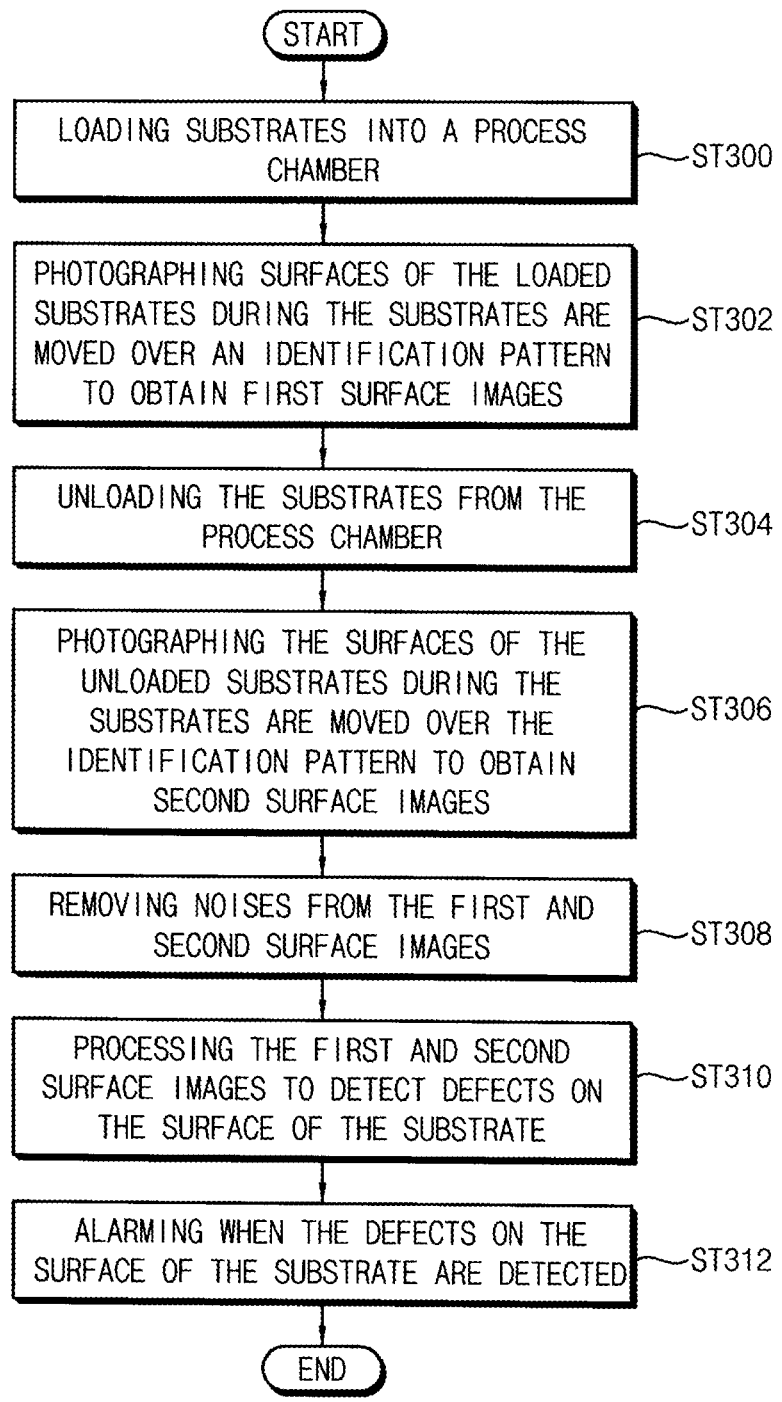

METHOD OF INSPECTING A SURFACE OF A SUBSTRATE AND APPARATUS FOR PERFORMING THE SAME

CROSS-RELATED APPLICATION

This application claims priority under 35 USC §119 to Korean Patent Application No. 2013-130794, filed on Oct. 31, 2013 in the Korean Intellectual Property Office (KIPO), the contents of which are herein incorporated by reference in their entirety.

BACKGROUND

1. Field

Example embodiments relate to a method of inspecting a surface of a substrate and an apparatus for performing the same. In one or more example embodiments, the surface may be the surface of a semiconductor substrate.

2. Description of the Related Art

Generally, an apparatus for inspecting a surface of a semiconductor substrate may include a chamber, a photographing unit and an image-processing unit. The photographing unit may be arranged in the chamber to photograph the surface of the semiconductor substrate. The image-processing unit may process an image obtained from the photographing unit to detect defects on the surface of the semiconductor substrate.

According to related arts, the inspecting apparatus may be separated from a processing chamber that manufactures a semiconductor device including the semiconductor substrate. Thus, it may be required to transfer the semiconductor substrates from the processing chamber to the inspecting apparatus. Therefore, a time for inspecting the surface of the semiconductor substrate may be relatively long. To decrease this inspection time, only some semiconductor substrates among all of the semiconductor substrates may be selected for inspection. As a result, the inspecting test may not be performed on the non-selected semiconductor substrates. These non-selected semiconductor substrates may have an abnormal surface. The abnormal surface of the semiconductor substrate may cause faults in following processes.

SUMMARY

Example embodiments provide a method of inspecting surfaces of all of substrates during a process may be performed on the substrates.

Example embodiments also provide an apparatus for performing the above-mentioned method.

According to example embodiments, there may be provided a method of inspecting a surface of a substrate. In the method of inspecting the surface of the substrate, a first surface image of the substrate before loaded into a process chamber may be obtained. The first surface image may be processed to detect a defect on the surface of the substrate.

In example embodiments, processing the first surface image may include removing noises from the first surface image.

In example embodiments, the method may further include obtaining a second surface image of the substrate after unloaded from the process chamber, and processing the second surface image to detect a defect on the surface of the substrate.

In example embodiments, obtaining the second surface image may include sensing the substrate after unloaded from the process chamber.

In example embodiments, sensing the substrate unloaded from the process chamber may include detecting a section where the substrate may be moved over an identification pattern having a structure different from that of the surface of the substrate.

In example embodiments, obtaining the first surface image may include sensing the substrate loaded into the process chamber.

In example embodiments, sensing the substrate loaded into the process chamber may include detection a section where the substrate may be moved over an identification pattern having a structure different from that of the surface of the substrate.

According to example embodiments, there may be provided an apparatus for inspecting a surface of a substrate. The apparatus may include a photographing unit and an image-processing unit. The photographing unit may photograph the surface of the substrate before loaded into a process chamber and after unloaded from the process chamber to obtain surface images of the substrate. The image-processing unit may process the surface images of the substrate to detect defects on the surface of the substrate.

In example embodiments, the apparatus may further include an identification pattern positioned under between the substrate and the process chamber. The identification pattern may have a structure different from that of the surface of the substrate. The photographing unit may sense the substrate loaded into the process chamber and unloaded from the process chamber.

In example embodiments, the identification pattern may include a shade pattern. The shade pattern may include a bar code.

In example embodiments, the image-processing unit may include a noise-removing member configured to remove noises from the surface images.

In example embodiments, the image-processing unit may include an alarming member configured to alarm when the defect on the surface of the substrate may be detected.

According to example embodiments, the photographing unit adjacent to the process chamber may photograph the surfaces of all of the substrates before loaded into the process chamber and after unloaded from the process chamber. Thus, the surfaces of all of the substrate may be inspected during a process may be performed without transferring the substrates. Further, it may not be required to stand by the substrates on which the inspection test may be performed so that a time for manufacturing a semiconductor device including the substrate may be remarkably reduced. Particularly, the surface image of the substrate may be obtained using the identification pattern. Therefore, it may not be required to use an additional sensor configured to sense the substrate.

At least one example embodiment relates to a method of inspecting a substrate

In some example embodiment, the method includes first capturing, via an image sensor, a first image of a surface of the substrate as a robot is loading the substrate into a process chamber; first detecting, by an image processor, defects on the surface of the substrate based on the first image, the detecting being performed before the substrate undergoes processing in the process chamber; and first determining, by the image processor, whether to instruct the process chamber to process the substrate based on the detecting.

In some example embodiments, the method further includes second capturing, via the image sensor, a second image of the surface of the substrate as a robot is unloading the substrate from the process chamber; second detecting, by the image processor, defects on the surface of the substrate based on the second image, the detecting being performed after the substrate undergoes processing in the process chamber; and second determining, by the image processor, whether to one or more of trigger an alarm, discard the substrate and reload the substrate into the process chamber for further processing based on the second detecting.

In some example embodiments, the image sensor is configured to continually sense an area adjacent to the process chamber, and the image processing unit is configured to determine that the robot is one of loading and unloading the substrate based on the continual sensing of the area.

In some example embodiments, the area adjacent to the process chamber includes a distinct pattern identifiable by the image processor, and the image processing unit is configured to determine that the robot is loading or unloading the substrate based on whether the image sensor senses the distinct pattern.

In some example embodiments, the substrate is a semiconductor substrate, and the first detecting is performed inline with the loading of the substrate into the process chamber.

BRIEF DESCRIPTION OF THE DRAWINGS

Example embodiments will be more clearly understood from the following detailed description taken in conjunction with the accompanying drawings. FIGS. 1 to 10 represent non-limiting, example embodiments as described herein.

FIG. 1 is a perspective view illustrating an apparatus for inspecting a surface of a substrate in accordance with example embodiments;

FIG. 2 is a flow chart illustrating a method of inspecting a surface of a substrate using the apparatus in FIG. 1;

FIG. 3 is a perspective view illustrating an apparatus for inspecting a surface of a substrate in accordance with example embodiments;

FIGS. 4 to 6 are perspective views illustrating operations of a photographing unit configured to photograph the substrate loaded into a process chamber;

FIGS. 7 to 9 are perspective views illustrating operations of the photographing unit configured to photograph the substrate unloaded from the process chamber; and FIG. 10 is a flow chart illustrating a method of inspecting a surface of a substrate using the apparatus in FIG. 3.

DETAILED DESCRIPTION OF EXAMPLE EMBODIMENTS

Figure 1:
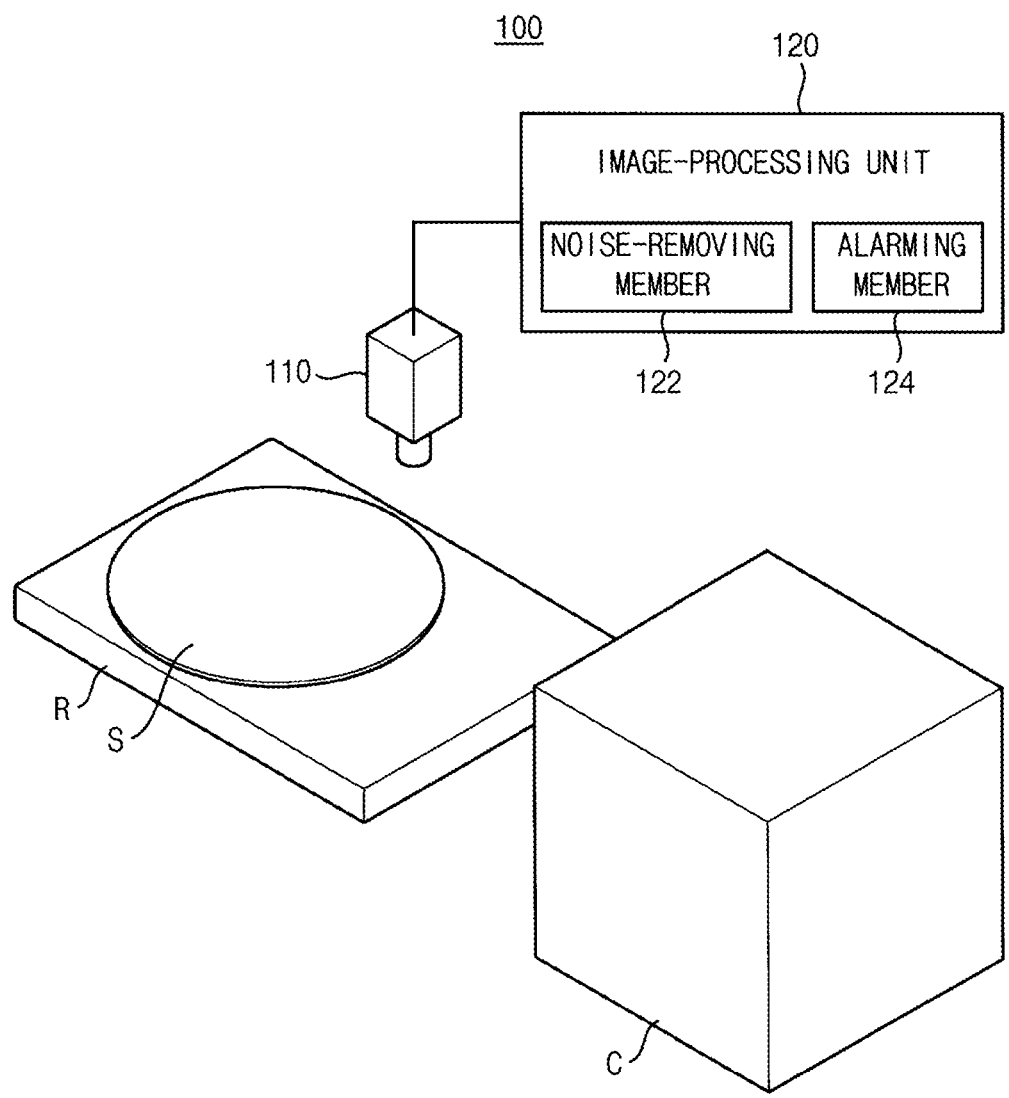

Various example embodiments will be described more fully hereinafter with reference to the accompanying drawings, in which some example embodiments are shown. Example embodiments may, however, be embodied in many different forms and should not be construed as limited to the example embodiments set forth herein. Rather, these example embodiments are provided so that this disclosure will be thorough and complete, and will fully convey the scope of the example embodiments to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the example embodiments.

Unless otherwise defined, all terms (including technical and scientific terms) used herein have the same meaning as commonly understood by one of ordinary skill in the art to which these example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

FIG. 1 is a perspective view illustrating an apparatus for inspecting a surface of a substrate in accordance with example embodiments.

Referring to FIG. 1, an apparatus 100 for inspecting a surface of a substrate may include a photographing unit 110 and an image-processing unit 120.

In example embodiments, a robot R may load the substrate S into a process chamber C. The process chamber C may process the loaded substrate S. Thereafter, the robot R may unload the substrate S from the process chamber C. The process chamber C may include a deposition chamber, an exposure chamber, an etch chamber, etc. The substrate S may include a semiconductor substrate, a glass substrate, etc.

The photographing unit 110 may be arranged adjacent to the process chamber C. The photographing unit 110 may photograph the surface of the substrate S before loaded into the process chamber C to obtain a first surface image of the substrate S before the process chamber C processes the substrate S. The photographing unit 110 may photograph the surface of the substrate S after unloaded from the process chamber C to obtain a second surface image of the substrate S after the process chamber C processes the substrate S. In example embodiments, the photographing unit 110 may photograph the surface of the substrate S by a line scanning technique, however, example embodiments are not limited thereto.

In example embodiments, because the photographing unit 110 may be positioned adjacent to the process chamber C, an inspection process may be performed on the substrates S without transferring the substrates S to a separate lot such that the inspecting apparatus 100 may operate without operator assistance. Therefore, a time for manufacturing a semiconductor device including the substrate S may be reduced.

In example embodiments, the photographing unit 110 may photograph all of the substrates S loaded into the process chamber C and unloaded from the process chamber C to obtain the first surface images and the second surface images, respectively. That is, the surface images of all of the substrates S, which may be processed in the process chamber C, may be obtained by the photographing unit 110. Thus, all of the substrates S may be inspected using the apparatus 100.

The first surface images and the second surface images obtained by the photographing unit 110 may be transmitted to the image-processing unit 120. The image-processing unit 120 may process the first surface images and the second surface images to determine whether the substrates S contain defects. By processing both the first surface images and the second surface images, the image-processing unit 120 may detect defects on the surfaces of the substrate S before and after the processing by the process chamber C. As a result, the apparatus 100 may inspect the surfaces of the substrates S in real time while the processing by the process chamber C is performed.

The image-processing unit 120 includes a processor and a memory (not shown).

The processor may be configured to carry out instructions of a computer program by performing the arithmetical, logical, and input/output operations. The processor may read the instructions from the memory via a bus and/or a network interface. The processor may be a logic chip, for example, a central processing unit (CPU), a controller, or an application-specific integrated circuit (ASIC), that when, executing the instructions stored in the memory, configures the processor as a special purpose machine. More specifically, the instructions may configure the processor as a noise-removing member 122 and an alarming member 124, which will be described later with reference to FIG. 2 and other pertinent drawings.

The memory may be a non-transitory computer readable storage medium. The memory may include a random access memory (RAM), read only memory (ROM), and/or a permanent mass storage device, such as a disk drive.

In example embodiments, the image-processing unit 120 may include a noise-removing member 122 and an alarming member 124. The noise-removing member 122 may remove noises such as a background image from the surface images. The alarming member 124 may trigger an alarm when the defects are detected on the surfaces of the substrates S.

In one or more example embodiments, in addition to triggering the alarm, the inspecting apparatus 100 may discard the substrates S in which the defects are detected.

In one or more example embodiments, in addition to triggering the alarm, the inspecting apparatus 100 may send the substrates S in which the defects are detected back to the processing chamber C for further processing.

Figure 2:
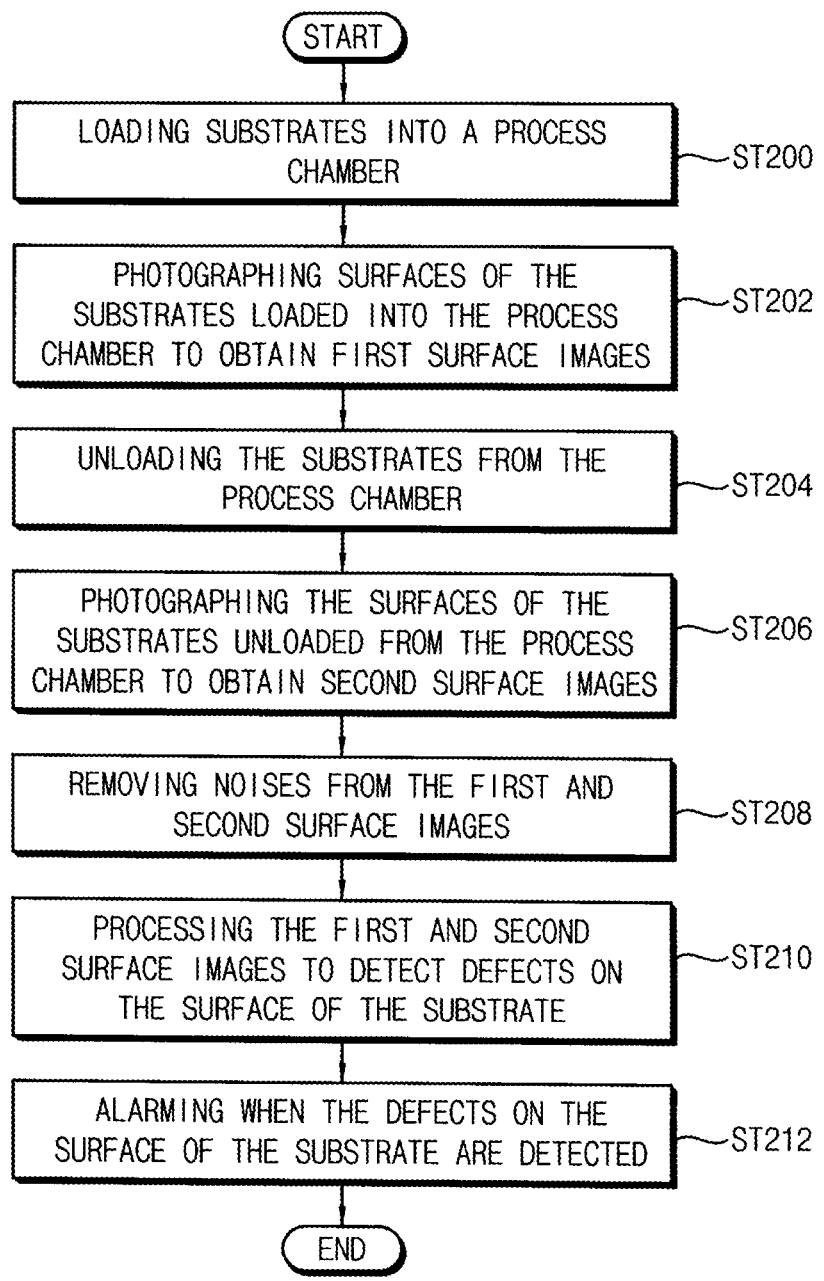

FIG. 2 is a flow chart illustrating a method of inspecting a surface of a substrate using the apparatus in FIG. 1.

Referring to FIGS. 1 and 2, in operation ST200, the robot R may sequentially load the substrates S into the process chamber C.

In operation ST202, the photographing unit 110 may photograph the surfaces of the substrates S loaded into the process chamber to obtain the first surface images of the substrates S. Because the photographing unit 110 may be positioned adjacent to the process chamber C, an inspection process may be performed on the substrates S without transferring the substrates S to a separate lot such that the inspecting apparatus 100 may operate without operator assistance.

In operation ST204, after the process may be performed on the substrates S, the robot R may unload the substrates S from the process chamber C.

In operation ST206, the photographing unit 110 may photograph the surfaces of the substrate S unloaded from the process chamber C to obtain the second surface images of the substrates S. Because the photographing unit 110 may be positioned adjacent to the process chamber C, an inspection process may be performed on the substrates S without transferring the substrates S to a separate lot such that the inspecting apparatus 100 may operate without operator assistance.

In operation ST208, the noise-removing member 122 may remove noises such as a background image from the first surface images and the second surface images.

In operation ST210, the image-processing unit 122 may process the first surface images and the second surface images to detect defects on the surfaces of the substrates S. In example embodiments, the first surface images and the second surface images may correspond to images of the entire substrates S processed in the process chamber C. Thus, all of the substrates S may be inspected using the apparatus 100.

In operation ST212, if the defects are detected, the alarming member 124 may trigger an alarm. The alarm may be an audible or a visual alarm. Further, the alarming member 124 may alert an operation of the alarm via updating a log file.

Figure 3:
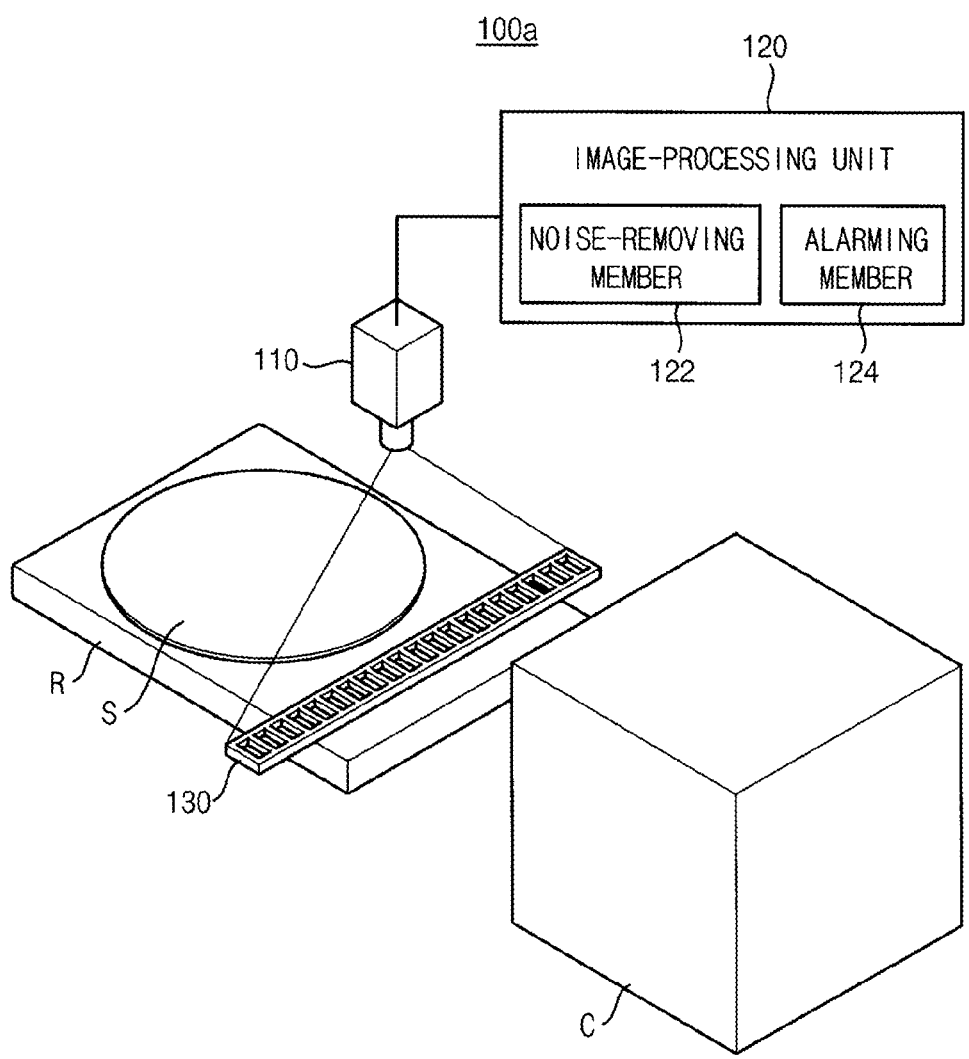

FIG. 3 is a perspective view illustrating an apparatus for inspecting a surface of a substrate in accordance with example embodiments.

Referring to FIG. 3, an apparatus 100a for inspecting a surface of a substrate in accordance with this example embodiment may include elements substantially the same as those of the apparatus 100 in FIG. 1 except for further including an identification pattern 130. Thus, the same reference numerals may refer to the same elements and any further illustrations with respect to the same elements may be omitted herein for brevity.

The identification pattern 130 may be positioned between the process chamber C and the photographing unit 110. The identification pattern 130 may be placed under a horizontal plane where the robot R may be moved.

The identification pattern 130 may be used for sensing the substrate S loaded into the process chamber C and unloaded from the process chamber C. The identification pattern 130 may have a structure different from that of the surface of the substrate S. For example, the identification pattern 130 may include a shade pattern having regularly or irregularly arranged shades.

As mentioned above, because the photographing unit 110 may continuously photograph a front region of the process chamber C corresponding to a loading position and an unloading position of the substrate S in the line scan technique, a straight line of the shades on the identification pattern 130 may correspond to a line scan direction of the photographing unit 110. When the substrate S transferred by the robot R may be positioned over the identification pattern 130, the substrate S may cover the identification pattern 130. Thus, the photographing unit 130 may photograph the substrate S, not the identification pattern 130. After the substrate S may be moved over the identification pattern 130, the photographing unit 110 may again photograph the identification pattern 130. Because an image of the identification pattern 130 having the shades may be different from the surface image of the substrate S, the loading or the unloading of the substrate S may be detected based on a difference between the image of the identification pattern 130 and the surface image of the substrate S. The identification pattern 130 may include an optical machine-readable representation of data (e.g., a bar code).

Figure 4:
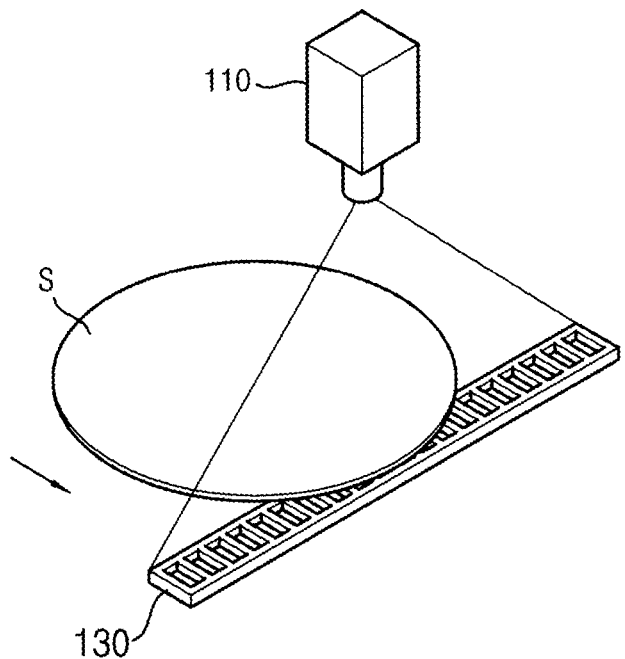
Figure 5:
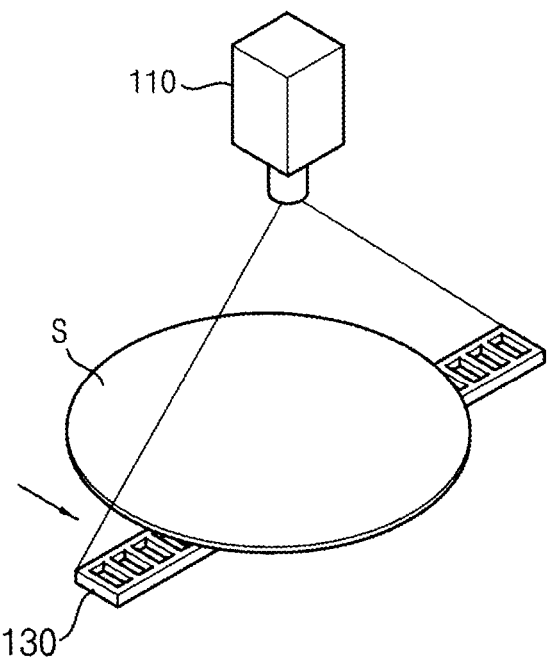
Figure 6:
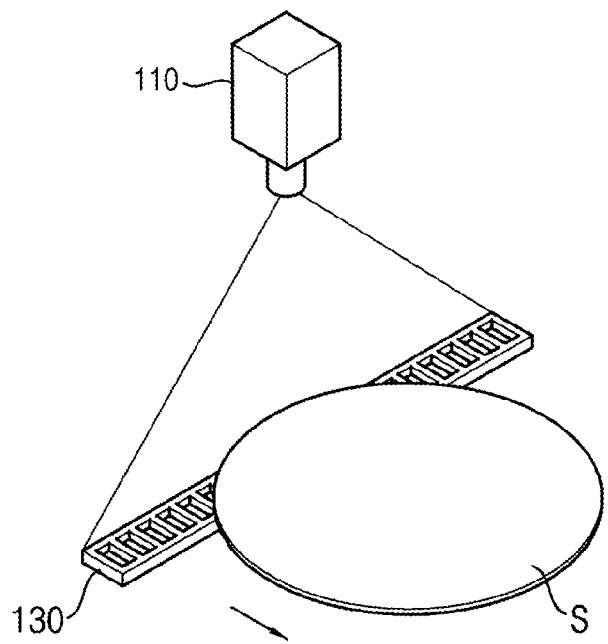

FIGS. 4 to 6 are perspective views illustrating operations of a photographing unit configured to photograph the substrate loaded into a process chamber.

Referring to FIGS. 4 to 6, as illustrated in FIG. 4, when the substrate S is loaded, by the robot R, into the process chamber C from a right side thereof, a right portion of the substrate S may cover the identification pattern 130.

As illustrated in FIG. 5, as the robot R continues to load the substrate S, a central portion of the substrate S may cover the identification pattern 130.

As illustrated in FIG. 6, as the robot R further loads the substrate S from a left side of the process chamber C, a left portion of the substrate S may be moved over the identification pattern 130, the identification pattern 130 may be exposed to the photographing unit 110. An image photographed by the photographing unit 110 from a point when the right portion of the substrate S may cover the identification pattern 130 to a point when the left portion of the substrate S may not cover the identification pattern 130 may correspond to the first surface image of the substrate S. The first surface image may correspond to a surface image of the substrate S before the process chamber C processes the substrate S.

Figure 7:
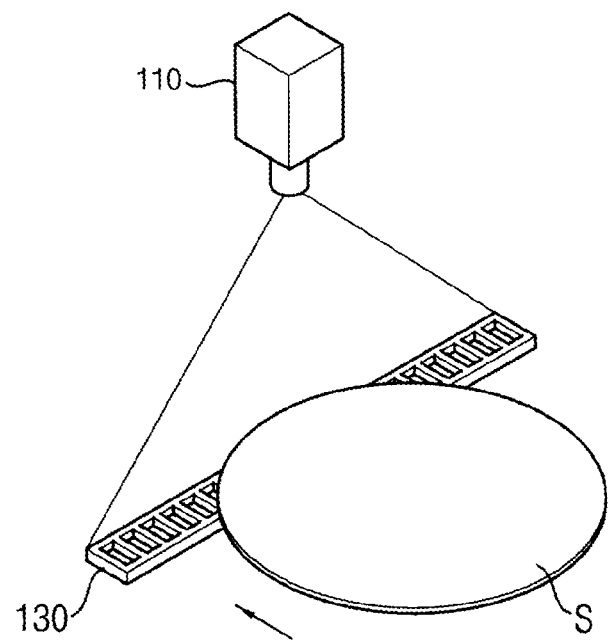
Figure 8:
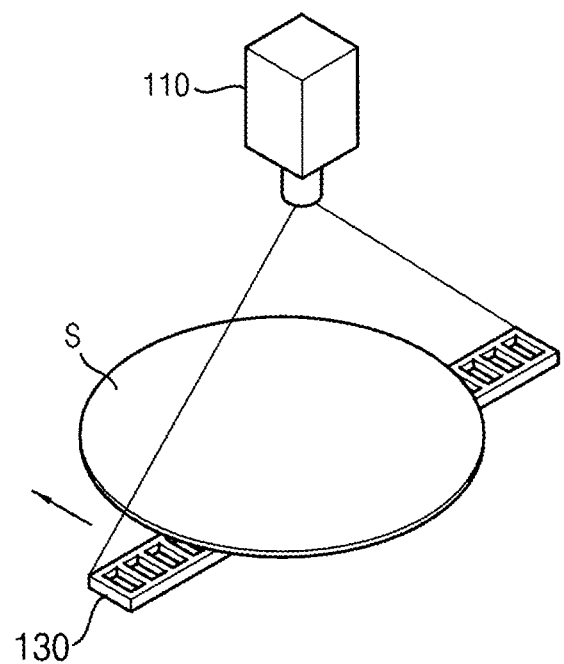
Figure 9:
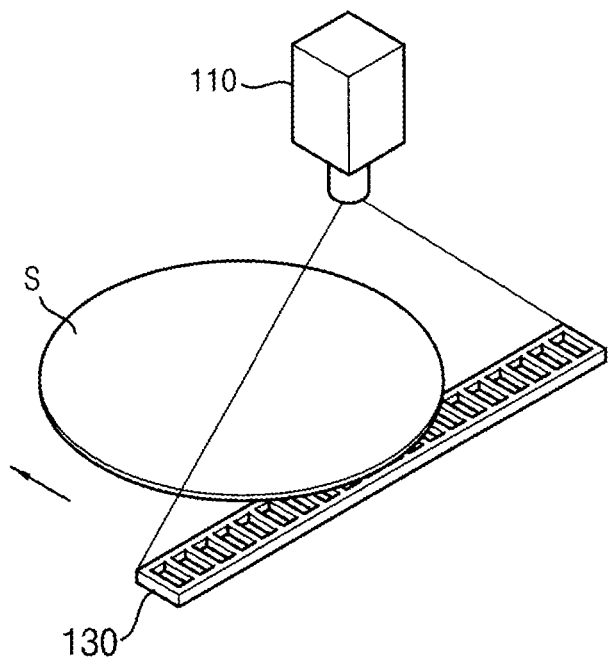

FIGS. 7 to 9 are perspective views illustrating operations of the photographing unit configured to photograph the substrate unloaded from the process chamber.

Referring to FIGS. 7 to 9, as illustrated in FIG. 7, when the substrate S may be unloaded from the process chamber C in a left direction by the robot R, the left portion of the substrate S may cover the identification pattern 130.

As illustrated in FIG. 8, as the robot R continues to unload the substrate S, the central portion of the substrate S may cover the identification pattern 130.

As illustrated in FIG. 9, as the robot R further unloads the substrate S, the identification pattern 130 may be exposed to the photographing unit 110. An image photographed by the photographing unit 110 from a point when the left portion of the substrate S may cover the identification pattern 130 to a point when the right portion of the substrate S may not cover the identification pattern 130 may correspond to the second surface image of the substrate S. The second surface image may correspond to a surface image of the substrate S after the process.

In example embodiments, the surface image of the substrate S may be obtained using the identification pattern 130. Thus, the surface image of the substrate S may be accurately obtained without a sensor configured to sense the loading and the unloading of the substrate S. However, example embodiments are not limited thereto. For example, the apparatus 100 may include an electronic sensor (not illustrated) to detect the loading and the unloading of the substrate S.

FIG. 10 is a flow chart illustrating a method of inspecting a surface of a substrate using the apparatus in FIG. 3.

Referring to FIGS. 3 and 10, in operation ST300, the robot R may sequentially load the substrates S into the process chamber C.

In operation ST302, the photographing unit 110 may photograph the surfaces of the substrates S loaded into the process chamber C to obtain the first surface images of the substrates S. The first surface image may correspond to an image photographed by the photographing unit 110 as the substrate S is loaded into the process chamber C and moves over the identification pattern 130.

In operation ST304, after the process chamber processes the substrates S, the robot R may unload the substrates S from the process chamber C.

In operation ST306, the photographing unit 110 may photograph the surfaces of the substrate S unloaded from the process chamber C to obtain the second surface images of the substrates S. The second surface image may correspond to an image photographed by the photographing unit 110 as the substrate S is unloaded from the process chamber C and moves over the identification pattern 130.

In operation ST308, the noise-removing member 122 may remove noises such as a background image from the first surface images and the second surface images.

In operation ST310, the image-processing unit 122 may process the first surface images and the second surface images to detect defects on the surfaces of the substrates S. In example embodiments, the first surface images and the second surface images may correspond to images of the entire substrates S processed in the process chamber C.

In operation ST312, when the defects may be detected, the alarming member 124 may trigger the alarm.

According to example embodiments, the photographing unit 110 adjacent to the process chamber may photograph the surfaces of all of the substrates before the substrates S are loaded into the process chamber C and after unloaded from the process chamber. Further, because the surfaces of all of the substrate S may be inspected without transferring the substrates S, the inspecting apparatus 100 may operate without operator assistance. Therefore, the inspection test may be performed so that a time for manufacturing a semiconductor device including the substrate may be reduced. Additionally, the surface image of the substrate may be obtained using the identification pattern 130. Therefore, the apparatus 100 may detect the defects without using an additional sensor configured to sense the substrate.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the example embodiments. Accordingly, all such modifications are intended to be included within the scope of the example embodiments defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of inspecting a surface of a substrate as the substrate is loaded and unloaded from a front region of a process chamber, the method comprising:
   continually photographically monitoring an identification pattern adjacent to the front region of the process chamber, the identification pattern having a structure different from the surface of the substrate;
   sensing that the substrate is being loaded into the process chamber based on whether the identification pattern is occluded by the substrate;
   obtaining a first surface image of the substrate as the substrate is loaded into the process chamber based on the sensing; and
   processing, by an image processor, the first surface image to detect defects on the surface of the substrate before the substrate undergoes processing in the process chamber.

2. The method of claim 1, wherein processing the first surface image comprises:
   removing noises from the first surface image.

3. The method of claim 1, further comprising:
   obtaining a second surface image of the substrate after the substrate is unloaded from the process chamber; and
   processing, by the image processor, the second surface image to detect the defects on the surface of the substrate after the substrate undergoes the processing in the process chamber.

4. The method of claim 3, wherein the processing the second surface image comprises:
   removing noises from the second surface image using the image processor.

5. The method of claim 3, wherein the obtaining the second surface image comprises:
   sensing that the substrate is being unloaded from the process chamber based on whether the identification pattern is occluded by the substrate.

6. The method of claim 1, wherein the substrate comprises:
   a semiconductor substrate.

7. An apparatus for inspecting a surface of a substrate as the substrate is loaded and unloaded from a front region of a process chamber, the apparatus comprising:
   an image sensor configured to continually photographically monitor an identification pattern adjacent to the front region of the process chamber, the identification pattern having a structure different from the surface of the substrate; and
   a processor configured to,
      sense that the substrate is being loaded into the process chamber and is being unloaded from the process chamber based on whether the identification pattern is occluded by the substrate,
      obtain surface images of the surface of the substrate, if the processor senses that the substrate is being loaded and unloaded, and
      process the surface images to detect defects on the surface of the substrate.

8. The apparatus of claim 7, wherein the identification pattern comprises:
   a shaded pattern.

9. The apparatus of claim 8, wherein the shaded pattern comprises:
   an optical machine-readable code.

10. The apparatus of claim 7, wherein the processor is configured to filter the surface images to remove noises from the surface images.

11. The apparatus of claim 7, wherein the processor is configured to trigger an alarm when the defects on the surface of the substrate are detected.

12. A method of inspecting a substrate as the substrate is loaded and unloaded from a front region of a process chamber, the method comprising:
   continually sensing, by an image sensor, an area adjacent to the front region of the process chamber, the area adjacent to the process chamber including a distinct pattern identifiable by an image processor;
   determining, by the image processor, that a robot is one of loading and unloading the substrate based on whether the distinct pattern is occluded by the substrate;
   first capturing, via the image sensor, a first image of a surface of the substrate as the robot is loading the substrate into a process chamber;
   first detecting, by the image processor, defects on the surface of the substrate based on the first image, the first detecting being performed before the substrate undergoes processing in the process chamber; and
   first determining, by the image processor, whether to instruct the process chamber to process the substrate based on the first detecting.

13. The method of claim 12, further comprising:
   second capturing, via the image sensor, a second image of the surface of the substrate as the robot is unloading the substrate from the process chamber;
   second detecting, by the image processor, defects on the surface of the substrate based on the second image, the second detecting being performed after the substrate undergoes processing in the process chamber; and
   second determining, by the image processor, whether to one or more of trigger an alarm, discard the substrate, and reload the substrate into the process chamber for further processing based on the second detecting.

14. The method of claim 12, wherein the substrate is a semiconductor substrate, and the first detecting is performed inline with the loading of the substrate into the process chamber.

\* \* \* \* \*